United States Patent
Edlund (10) Patent No.: US 9,750,947 B2
(45) Date of Patent: Sep. 5, 2017

(54) POWER SAVING COMMUNICATION METHOD FOR AN IMPLANTABLE MEDICAL DEVICE

(71) Applicant: ST. JUDE MEDICAL AB, Jarfalla (SE)

(72) Inventor: Par Edlund, Sollentuna (SE)

(73) Assignee: St. Jude Medical AB, Jarfalla (SE)

( * ) Notice: Subject to any disclaimer, the term of this patent is extended or adjusted under 35 U.S.C. 154(b) by 269 days.

(21) Appl. No.: 14/190,518

(22) Filed: Feb. 26, 2014

(65) Prior Publication Data

US 2014/0180366 A1    Jun. 26, 2014

Related U.S. Application Data

(62) Division of application No. 13/504,115, filed as application No. PCT/SE2009/000473 on Oct. 27, 2009, now Pat. No. 8,700,153.

(51) Int. Cl.
*A61N 1/372* (2006.01)
*A61N 1/362* (2006.01)
(Continued)

(52) U.S. Cl.
CPC ....... *A61N 1/37276* (2013.01); *A61N 1/3622* (2013.01); *A61N 1/371* (2013.01); *A61N 1/3688* (2013.01)

(58) Field of Classification Search
CPC . A61N 1/37211; A61N 1/37276; A61N 1/378
See application file for complete search history.

(56) References Cited

U.S. PATENT DOCUMENTS

| 5,193,212 A | 3/1993 | Son |
| 6,893,395 B1 | 5/2005 | Kraus et al. |

(Continued)

FOREIGN PATENT DOCUMENTS

| EP | 1953922 A1 | 8/2008 |
| EP | 1655848 B1 | 11/2008 |
| WO | 2006116004 A1 | 11/2006 |

OTHER PUBLICATIONS

Restriction Requirement, mailed Aug. 21, 2013—U.S. Appl. No. 13/504,115.

(Continued)

*Primary Examiner* — Eric D. Bertram (57) ABSTRACT

A non-implantable communication unit conducts wireless communication with an implantable medical device (IMD). The communication unit comprises a request processor for generating power down requests destined to the IMD and triggering temporary power down of the IMD radio equipment. When the communication unit receives a data packet from the IMD or a connected programmer it determines the size of the data packet. A timer processor sets a timer to a value defined based on the determined size. A processor controller selectively controls the operation of request processor to generate or stop generating the power down requests based on a current value of the timer. Power down of the IMD radio equipment is thereby prevented if it is likely that the IMD comprises data to transmit to the communication unit as predicted based on data packet sizes.

8 Claims, 6 Drawing Sheets

(51) Int. Cl.
*A61N 1/37* (2006.01)
*A61N 1/368* (2006.01)

(56) References Cited

U.S. PATENT DOCUMENTS

| | | |
|---|---|---|
| 2002/0016568 A1 | 2/2002 | Lebel et al. |
| 2003/0114897 A1 | 6/2003 | Von Arx et al. |
| 2005/0195930 A1* | 9/2005 | Spital ............... A61M 5/14244 375/368 |
| 2005/0240245 A1 | 10/2005 | Bange et al. |
| 2005/0283207 A1 | 12/2005 | Hochmair et al. |
| 2007/0049991 A1 | 3/2007 | Klostermann et al. |
| 2009/0248116 A1 | 10/2009 | Le Reverend et al. |
| 2009/0290525 A1 | 11/2009 | Kekalainen et al. |

OTHER PUBLICATIONS

NonFinal Office Action, mailed Oct. 23, 2013—U.S. Appl. No. 13/504,115.

Notice of Allowance, mailed Feb. 4, 2014—U.S. Appl. No. 13/504,115.

* cited by examiner

POWER SAVING COMMUNICATION METHOD FOR AN IMPLANTABLE MEDICAL DEVICE

CROSS REFERENCE TO RELATED APPLICATIONS

This application is a division of U.S. patent application Ser. No. 13/504,115, filed Apr. 25, 2012, now U.S. Pat. No. 8,700,173.

TECHNICAL FIELD

The present invention generally relates to wireless communication involving implantable medical devices, and in particular to controlling wireless communication between an implantable medical device and a non-implantable communication unit.

BACKGROUND

The traditional approach of conducting communication with an implantable medical device (IMD) has been through usage of inductive telemetry. Nowadays, the communication technology within the field of IMDs is moving away from inductive telemetry towards radio frequency (RF) based telemetry or communication.

RF telemetry has several advantages over inductive telemetry including, for instance, higher bit rates and longer range. However, a drawback is that RF telemetry generally requires more power. IMDs are typically battery driven and therefore have limited operation life dictated by the power consumption of the IMDs. Utilizing RF telemetry as the communication protocol consequently causes an impact to the longevity of the IMDs.

In order to at least partly solve this problem of increased power consumption for RF-based communication sessions between IMDs and non-implantable communication units or modules, algorithms for reducing power have been developed. An example of such an algorithm is denoted power save and involves regularly turning off the radio equipment in the IMD for a certain time period, typically 20-30 ms, during a communication session. The power save algorithm is mainly based on the stream of intracardiac electrogram (IEGM) data that is sent periodically in a burst-like manner from the IMD. For instance and depending on the particular device design, IEGM samples can be produced by the IMD every 7.8125 ms. The IMD then preferably buffers a number of such IEGM samples, such as six, prior transmission. The buffering of IEGM samples yields a periodicity of, in this example, 6.times.7.8125=46.875 ms for the IEGM messages sent from the IMD to the non-implantable communication unit. Power saving can therefore be performed during those periods when the IMD buffers IEGM samples.

Though the power save algorithm reduces power consumption by turning off the IMD radio equipment several times during an ongoing communication session it may also, as a drawback, prolong the communication session. The net result may therefore in some cases not be a power reduction but actually increased total energy consumption for the whole communication session and thereby reduced longevity of the IMD.

U.S. Pat. No. 6,647,298 relates to saving power during the communication between an IMD and a non-implantable communication unit. The power saving is accomplished by selectively switching on and off the receiver of the IMD based on whether received signal strengths exceed a discriminator threshold.

US 2007/0150028 discloses a remote monitoring device interrogating an IMD on an intermittent basis over a wireless telemetry link, with interrogations being performed either according to a programmed schedule or upon receiving a command to do so via a user interface. Power management can optimize RF telemetry usage of the IMD by combining interrogations scheduled to occur at or near the same time into a single communications session.

SUMMARY

There is therefore a need for a technique that can be used in connection with power saving algorithms during IMD-based communication sessions but that does not unnecessarily prolong the total time for the communication session.

It is an objective to provide an improved data communication between an IMD and a non-implantable communication unit.

It is a particular objective to provide a selective activation and deactivation of power down of IMD radio equipment during a communication session.

These and other objectives are met by embodiments as defined by the accompanying patent claims.

Briefly, a communication unit is capable of wireless communication with an IMD using RF telemetry. The communication unit consequently comprises a receiver for receiving data packets transmitted by the IMD and a transmitter for transmitting data packets to the IMD. A power down processor is implemented in the communication unit for generating power down requests destined to the IMD and triggering a power down of at least one of a transmitter and a receiver in the IMD. The power down requests thereby cause a temporary shutdown of the IMD radio equipment in order to save power of the battery-driven IMD during an ongoing communication session.

The power down requests should not be generated and transmitted to the IMD if it is likely that the IMD comprises data that it needs to transmit to the communication unit. The communication unit consequently predicts, based on data packet sizes, whether it is likely that the IMD comprises such data. A size processor is arranged in the communication unit for determining the size of data packets received from the IMD or that are transmitted to the IMD and preferably originate from a connected data processing unit. The determined size is utilized by a timer processor to set the value of at least one timer. A processor controller is arranged connected to the power down request processor and controls the operation of the request processor based on the current value of the at least one timer. Thus, the processor controller selectively controls the power down request processor to generate or stop generating the power down requests based on the current value of the at least one timer.

The size-based control of the power down requests is based on the theory that the communication unit can predict, from the size of a data packet, whether it is likely that the IMD will transmit further data to the communication unit within an immediate following time window. For instance, the size of a data packet from the data processing unit can be used to discriminate between data requests and acknowledgements (ACKs). The former will cause the IMD to generate and transmit response data and therefore power down of the IMD radio equipment should be postponed for a period of time to allow the IMD time to transmit the response data. The timer is therefore set to a value to allow such data transmission before power down is initiated. However, in the case of ACKs it is less likely that the IMD comprises data to transmit and therefore the timer can be set to a different value to indicate that the power down procedure can be started earlier. Correspondingly, the size of data packets from the IMD can be used to discriminate between response data packets and ACKs and can additionally be used to predict whether a response data packet carries the last response data in the case of response data fragmentation.

An aspect also relates to a communication control method that involves determining the size of a data packet provided in the communication unit and originating from the IMD or the data processing unit. At least one timer is set to a value defined based on the data packet size. Selective control of the generation of power down requests is conducted based on the current value of the timer.

Embodiments of the invention will reduce the total time of a communication session utilizing a power saving procedure involving a temporary and typically periodic power down of the IMD radio equipment. Reducing the total time of the communication session will reduce the total power or energy consumption of the IMD for the session and thereby increase the longevity of the IMD. Additionally, faster interrogation of IMDs is achieved as requested data can be faster delivered from the IMD without any interruption in the data delivery due to radio equipment power downs.

Embodiments can also be implemented without any modifications to the IMD and are therefore compatible with existing IMDs.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present invention is generally related to data communication between an implantable medical device (IMD) and a non-implantable communication unit. More particularly, the invention is directed towards techniques for shortening the time duration of a radio frequency (RF) communication session involving the IMD and the non-implantable communication unit.

Figure 1:
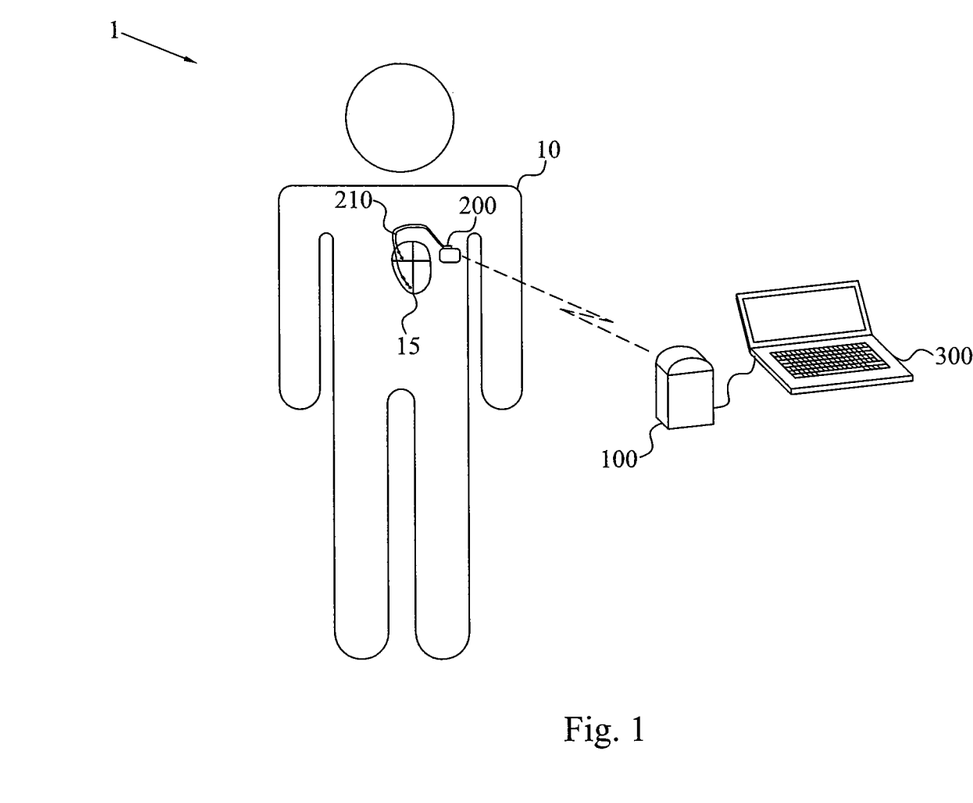
FIG. 1 is a schematic overview of an embodiment of a data communication system comprising an implantable medical device, a non-implantable communication unit and a data processing unit.

FIG. 1 is a schematic overview of a data communication system 1 according to an embodiment. The data communication system 1 comprises an IMD 200, illustrated as being implanted in a human body 10 in the figure. The IMD 200 of the embodiments can actually be any implantable medical device capable of delivering therapy to an animal, preferably mammalian and more preferably human body 10, and/or capable of recording physiological data and parameters from the body 10. The figure non-limitedly illustrates the IMD 200 as a device monitoring and/or providing therapy to the patient's heart 15 and consequently comprises one or more connectable cardiac leads 210 provided in or in connection to one or more ventricles and/or atriums of the heart 15. The IMD 200 could therefore be a pacemaker, defibrillator or cardioverter. However, the present invention is not limited to cardiac-associated IMDs 200 but may also be practiced with other implantable medical devices 200, such as drug pumps, neurological stimulators, physical signal recorders, oxygen sensors, or the like. The important feature of the IMD 200 is that is contains equipment capable of conducting wireless RF-based communication with the communication unit 100 of the data communication system 1.

The communication unit 100 operates as a base station of the data communication system 1 in that it constitutes the interface between the IMD 200 and an external instrument or data processing unit 300, such as a programmer for the IMD 200. This means that the communication unit 100 contains the equipment for effecting the wireless RF-based communication with the IMD 200 on behalf of the data processing unit 300. Thus, data requests from the data processing unit 300 are processed and packed into data packets and transmitted to the IMD 200 by the communication unit 100. Additionally, data packets received from the IMD 200 by the communication unit 100 can be forwarded to the data processing unit 300 for further processing and/or display therein.

Figure 2:
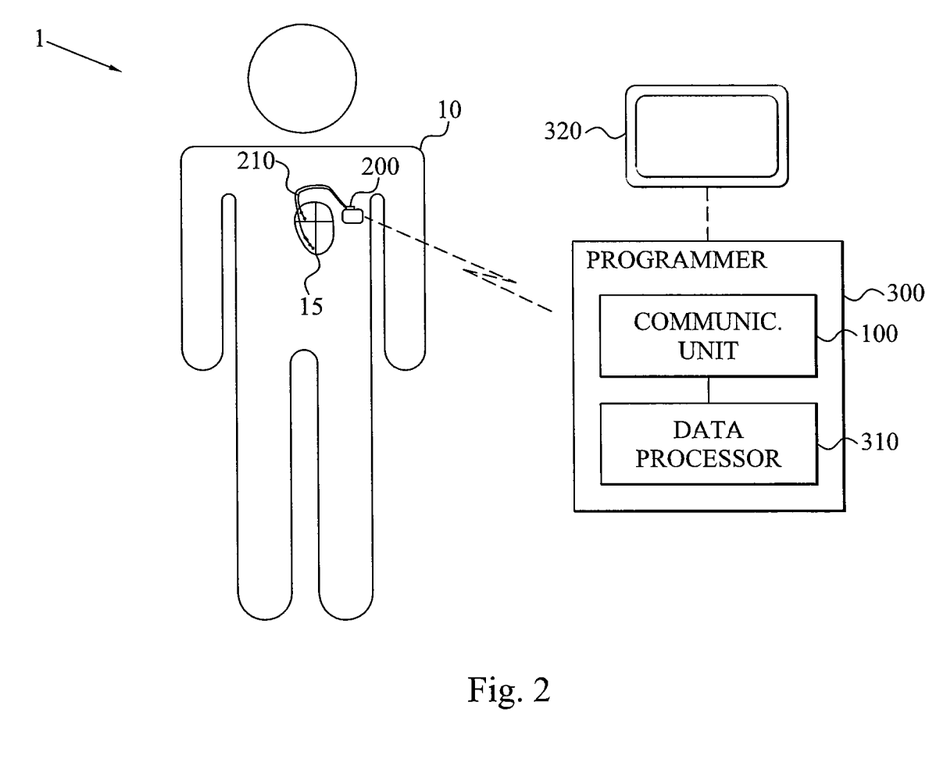
FIG. 2 is a schematic overview of another embodiment of a data communication system comprising an implantable medical device and a programmer.

The communication unit 100 and the data processing unit 300 can be separate devices as illustrated in FIG. 1, either wired connected or using a wireless connection, such as Bluetooth®, an infrared (IR) connection or a RF connection. In an alternative embodiment, as illustrated in FIG. 2, the functionality and equipment of the communication unit 100 and the data processing part of the data processing unit, here illustrated by a data processor 310, can be housed in a same device 300, such as a physician's programmer or workstation 300. The programmer 300 can additionally comprise or be connected to a display screen 320 for displaying the physiological data collected by the IMD 200 and wirelessly transmitted to the communication unit 100 and processed by the data processor 310 of the programmer 300.

RF-based communication with an IMD introduces new challenges as compared to inductive telemetry. Generally, RF telemetry requires more power than inductive telemetry, which will drain the battery driven IMD and can have a negative impact on the longevity and operation life of the IMD. Consequently, power saving algorithms applicable during an ongoing RF-based communication session have been developed. An example of such a power saving algorithm is to regularly turn off the radio equipment, i.e. transmitter and receiver, of the IMD during the communication session. This means that this equipment of the IMD will actually only consume power from the battery during a part of the whole time period of the communication session. The inventor has, though, realized that such a power saving algorithm can introduce new problems and disadvantages, which prolong the total time of the communication session and may, in certain cases, cause increased power consumption and reduced longevity for the IMD.

The present invention solves this problem of radio power down algorithms by making predictions at the non-implantable communication unit of whether the IMD comprises data to be transmitted to the non-implantable communication unit. In a basic embodiment, as long as the communication unit predicts that the IMD comprises data that should be transmitted to the non-implantable communication unit during the ongoing RF-based communication session, the communication unit should refrain from requesting the IMD to power down its radio equipment. In clear contrast, the data should be transmitted to the communication unit before the power saving algorithm triggers the IMD to power down the radio equipment. Correspondingly, once the communication unit predicts that the IMD no longer has any more data to transmit, the power saving algorithm can trigger a power down or even completely switch off of the IMD radio equipment unless the communication session should be ended.

The prediction conducted by the communication unit is performed based on the size of data packets received from the IMD and/or transmitted to the IMD, which is further described herein.

This conditional power down proposed by the embodiments reduces the risk of unnecessarily long communication sessions due to repeated power down periods even though data transmission could be effected. This also achieves a faster forwarding of requested or interrogated data to the data processing unit connected to the communication unit or in which the communication unit is implemented. Additionally, since the communication session can be ended earlier according to embodiments, the energy consumption in the IMD and also in the interrogating data processing unit and the communication unit can be decreased.

Figure 3:
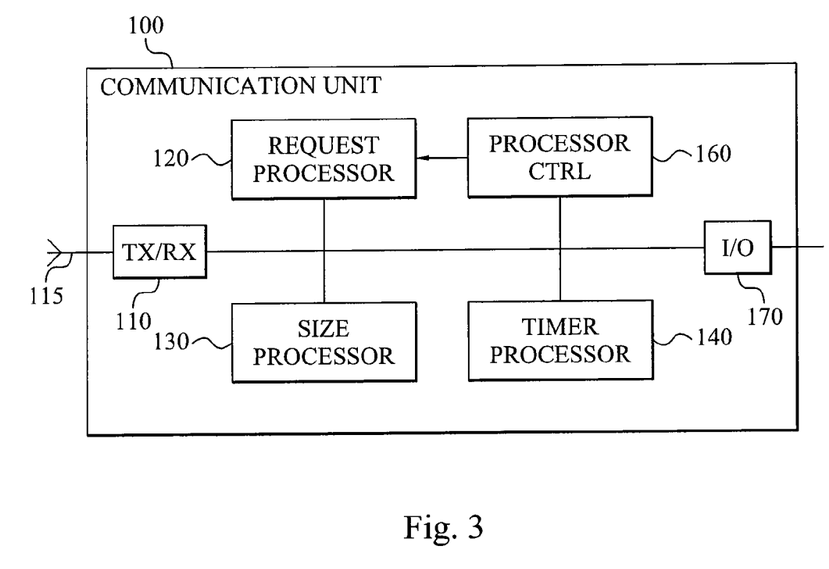
FIG. 3 is a schematic block diagram of a communication unit according to an embodiment.

FIG. 3 is a schematic block diagram of an embodiment of a communication unit 100 capable of conducting wireless RE-based communication with an IMD. The communication unit 100 in particular comprises a receiver 110 connected to a RE antenna 115 and arranged for receiving data transmitted by the IMD. Correspondingly, the communication unit 100 also comprises a transmitter 110 connected to a RF antenna 115 and arranged for wirelessly transmit data packets to the IMD. The receiver and transmitter 110 can be respective dedicated RF receiver and RF transmitter or represent the receiving branch and the transmitting branch of a combined RF transmitting and receiving unit or transceiver 110. The communication unit 100 can include one or more dedicated RF receiver antennas 115 connected to the receiver 110 and one or more dedicated RF transmitter antennas 115 connected to the transmitter 110. However, in most practical implementations one and the same RF antenna or antenna arrangement is connected to both the receiver and transmitter 110 or to the common transceiver.

The communication unit 100 also comprises a power down request processor 120 connected to the transmitter 110. The power down request processor 120 is responsible for generating the power down requests that are communicated to the IMD and cause a controller implemented therein to power down at least one of a transmitter and the receiver of the IMD. According to the invention this generation and transmission of power down requests is made conditional on the data packet size based predictions made by the communication unit 100 and therefore made conditional on the predictions whether the IMD has additional data to be transmitted to the communication unit 100.

A size processor 130 of the communication unit 100 is implemented to determine or estimate the size of data packets received by the receiver 110 and originating from the IMD and/or determine or estimate the size of data packets transmitted by the transmitter 110 to the IMD. In this context, the size of a data packet refers to the amount of data the data packet carries and is generally determined as a bit or byte length. Thus, the number of bytes occupied by a data packet is a suitable size parameter according to the embodiments and is preferably determined by the size processor 130.

In a first embodiment, the size processor 130 is arranged for only investigating the size of data packets originating from the IMD and received by the receiver 110. In an alternative embodiment, the size processor 130 instead only determines the size of data packets transmitted by the transmitter 110 to the IMD. However, it is preferred if the size processor 130 monitors and determines the size of both data packets transmitted to the IMD and received from the IMD.

A timer processor 140 is implemented in the communication unit 100 and is operational based on the determined size parameters from the size processor 130. The timer processor 140 sets a timer to a value defined based on the size parameter determined by the connected size processor 130. Thus, the actual value to which the timer processor 140 sets the timer is defined based on the size of a data packet received from the IMD or transmitted to the IMD.

A processor controller 160 of the communication unit 100 controls the operation of the power request processor 120 and the generation of the power down requests based on a current value of the timer set by the timer processor 140. Thus, the processor controller 160 thereby selectively controls the power down request processor 120 to generate or stop generating power down requests based on the timer value.

In more detail, in a preferred embodiment, the processor controller 160 generates a deactivation control command if the current value of the timer is different from a predefined stop value, such as zero. Thus, if the timer currently is not equal to the predefined stop value, the processor controller 160 deactivates and prevents the power down request processor 120 from generating a power down request destined to the IMD. The deactivation control command deactivates and prevents the request processor 120 from generating a power down request even if the communication unit 100 and the IMD are currently operating according to a power saving algorithm. In this embodiment, the communication unit 100 thereby predicts based on the timer value that the IMD comprises data that it needs to transmit to the communication unit 100 and should therefore allow the IMD time to send the data before powering down the IMD radio equipment.

Correspondingly, if the processor controller 160 confirms that the current value of the timer is equal to the predefined stop value, the processor controller 160 generates an activation control command. This activation control command triggers the power down request processor 120 to a new start the generation of power down requests that are transmitted to the IMD.

The timer-based and thereby size-based selective control of the power down request processor 120 contributes to a predictive decision of whether it is likely that the IMD will transmit any data to the communication unit 100 during a subsequent period of time.

The communication between the communication unit 100 and the IMD is preferably based on a request-response procedure. This means that the transmitter 110 of the communication unit transmits data requests to the IMD, which in turn responds by transmitting data responses generated based on the data requests. The data requests transmitted by the transmitter 110 are generated by a data processing unit and is forwarded to the communication unit 100 illustrated in FIG. 3 by a general input and output (I/O) unit 170. The I/O unit 170 operates as the interface between the communication unit 100 and the connected data processing unit. The I/O unit 170 can, in particular in the case of a wired connection, represent the equipment of the communication unit 100 allowing forwarding of data from the communication unit 100 to the data processing unit and vice versa over the wired connection. In the case of a wireless communication, the I/O unit 170 represents the equipment, such as transmitter/receiver and antenna, required in order to effectuate such a wireless data transfer.

The data processing unit then generates a request for data from the IMD that is forwarded to the communication unit 100 and wirelessly transmitted to the IMD. The IMD collects the requested data and returns it to the communication unit, which forwards the data to the data processing unit. Examples of such requested data include one or more physiological parameters monitored by the IMD in a human or animal body. The IMD consequently preferably comprises a sensor or other equipment for monitoring the physiological parameter and generating data samples representative of the value of the monitored parameter.

Another example of requested data includes IMD device or operation settings and other IMD device related information. As is well-known in the art, an IMD generally has several programmable operation parameters or settings that can be automatically determined by the IMD based on monitored physiological parameter or be determined by the physician and programmed into the IMD. Non-limiting examples of such parameter include AV delays, W delays, pacing pulse magnitudes, operation modes of IMD, etc. Examples of IMD device related information includes serial number, manufacture information, current battery status level, etc. Based on the reception of a data request from the communication unit, the IMD collects the relevant information of the IMD settings or status and includes this information in one or more response data packets.

Thus, when the data processing unit wants to retrieve data from the IMD, it compiles a data request and forwards it to the I/O unit 170. The size processor 130 preferably determines the size of the data request and provides information of the determined size to the timer processor 140. The timer processor 140 sets a value to the timer based on the determined size and the processor controller 160 investigates the timer value. Immediately following setting the timer value in response to receiving and size determining a data request, the timer value is different from the predefined stop value and consequently the processor controller 160 deactivates the power down request processor 120 to temporarily prevent the generation and transmission of a power down request.

The reason for the temporary prevention of power down of the IMD radio equipment is that it is expected that the data request transmitted by the transmitter 110 will shortly trigger the IMD to respond with one or more data packets generated in response to the data requests. Power down should therefore be temporarily stopped to allow the IMD to transmit this response data before power down its radio equipment.

The reason why the size processor 130 preferably determines the size of the data request from the I/O unit 170 is that the communication between the IMD and the data processing unit as conducted through the communication unit 100 is preferably acknowledged. This means that when the IMD has successfully received a data packet originating from the data processing unit so that the data packet can be decoded and processed by the IMD, it generates and transmits an acknowledgement (ACK) to the communication unit 100. The ACK is received by the receiver 110 and forwarded to the data processing unit by the I/O unit 170. Correspondingly, when the data processing unit has successfully received a response data packet from the I/O unit 170 and originating from the IMD, it generates an ACK that is forwarded to the I/O unit 170 and transmitted to the IMD by the transmitter 110.

The communication unit 100 consequently operates, in this context, as a base station or proxy server by forwarding data packets and ACKs between the IMD and the data processing unit. The communication unit 100 typically does not have the processing capability or equipment for parsing through data packets in order to determine what particular data they contain and what type of messages they are. Consequently, when receiving a data packet from the I/O unit 170 and destined to the IMD, the communication unit 100 generally does not know in advance whether the data packet is a data request or an ACK. In the former case, it is expected that response data will soon follow from the IMD and no power down should therefore be requested until the response data has been transmitted by the IMD. However, in the latter case it is plausible that the IMD already has transmitted all response data or at least a (major) portion thereof since the data processing unit has successfully received at least one data packet carrying such response data.

Since the communication unit 100 generally does not have message parsing functionality it instead determines the size of the transmitted data packets to thereby predict whether the data packet investigated is a data request which will trigger following IMD response(s) or an ACK generated based on a previously received data response from the IMD. Generally, the size of a data request is significantly larger than the size of an ACK. This means that the communication unit 100 can distinguish between data requests and ACKs through their sizes.

This means that if the size of a data packet received from the I/O unit 170 as determined by the size processor 130 exceeds a threshold size, the timer processor 140 concludes that it is likely that the data packet is indeed a data request. The timer should therefore be set at a timer value that gives the IMD sufficient time to respond to the data requests before the power down request processor 120 generates a next power down request. If the size of the data packet instead is below the threshold size as determined by the timer processor 140, the data packet from the I/O unit 170 is probably an ACK and therefore it is less likely that additional response data will be transmitted by the IMD. The timer processor 140 therefore sets the timer value to another value as compared to the case with large data packet size. If the timer is counted down as time lapses, the timer value will in this case be lower as compared to the case with data packets having a size exceeding the threshold. The lower timer value means that the timer will, within a shorter period of time, reach the predefined stop value, preferably zero, that indicates that power down requests can anew be generated and transmitted to the IMD.

Data packets having a comparatively larger size, i.e. estimated to correspond to data requests, should therefore trigger a comparatively longer deactivation period for the power down request processor 120 as compared to data packets having smaller sizes, i.e. estimated to correspond to ACKs.

A similar situation applies to the data packets received by the receiver 110 and forwarded to the data processing unit by the I/O unit 170. Thus, received data packets can in this context be data responses carrying response data generated by the IMD in response to a received data request. Alternatively, the received data packets can be ACKs transmitted by the IMD in response to a successfully received data request from the data processing unit. If a data packet received by the receiver 110 has a size as determined by the size processor 130 exceeding a threshold size, the timer processor 140 sets the timer to a value associated with a probable data response. Correspondingly, if the determined size of a received data packet is smaller than the threshold size and therefore likely an ACK, the timer processor 140 sets the timer to another value that will cause an earlier activation of the power down request processor 120 as compared to the larger timer value.

Data responses from the IMD can additionally be fragmented into several data packets. This particularly happens when transmitting recorded or determined physiological data that contains multiple data samples. The collected response data is too large to fit into a single response data packet. The IMD generally fills up data packets up to a defined maximum size and then has a final data packet that carries the rest of the response data. For instance, assume that the response data has a total size of 250 bytes and that the maximum payload size of a data packet is 100 bytes. A first response data packet carries the first 100 bytes of the response data and a second data packet comprises the following 100 bytes. The final 50 bytes are included in a third data packet. The size processor 130 determines the respective sizes of these data packets. With the first two data packets, the determined size corresponds to the maximum size for a data packet. The timer processor 140 thereby concludes that it is likely that more response data follows. The timer is therefore set, upon reception of each of the two first data packets, to value that prevents the power down request processor 120 to be activated by the processor controller 160 for a defined period of time to allow the IMD to transmit more data. However, the size of the third data packet indicates that it does not have the maximum allowed size. It is therefore unlikely that the IMD has additional data that needs to be transmitted as in such a case this additional data would be included in the third data packet. The timer value can therefore be set to a different, preferably lower value, as compared to the case with the two first data packets.

It is anticipated by this embodiment that in some situations, the last data packet in the case of fragmented response data can have a size equal to or close to the maximum allowed data packet size. The timer processor 140 will then set the timer to a value that triggers the processor controller 160 to deactivate the power down request processor 120 until the timer has reached the predefined stop value. Power down is therefore postponed longer than what is actually necessary. However, these cases will be rare in practice and the embodiments will in the vast majority of the practical situations lead to a more efficient communication session by preventing unnecessary or undesired power downs.

In a particular embodiment, the timer processor 140 has access to a single threshold size. In such a case, if the size of a data packet as determined by the size processor exceeds the threshold size, the timer processor 140 sets the value of the timer to a first value. Correspondingly, if the size is equal to or lower than the threshold size, the timer processor 140 instead sets the timer to a second, different value. In a preferred embodiment, the first value is larger than the second value. Thus, counting down the timer value until the predefined stop value, preferably zero, will take a comparatively longer period of time for the first timer value and therefore for larger data packet sizes as compared to the second timer value and comparatively smaller data packet sizes. In the former case, the longer period until the power down request processor 120 becomes activated by the processor controller 160 is due to the predicted likelihood of reception by the communication unit 100 of one or more data packets from the IMD since the larger data packet size indicates that a newly transmitted data packet probably is a data request or a newly received data packet is not the last response data packet in the case of fragmented data response.

In a preferred embodiment, both the first and second timer values are different from the predefined stop value. This means that even if the receiver 110 receives an ACK or a probable last response data packet or the transmitter 110 transmits an ACK, the power down request processor 120 is not immediately activated. In an alternative embodiment, the second timer value is though equal to the predefined stop value, which means that the power down request processor 120 can immediately generate a power down request that is transmitted to the IMD.

In an alternative approach more than one threshold size is employed. For instance, a first threshold size could be equal to or close to the maximum allowed data packet size. If a received or transmitted data packet exceeds the first threshold size, the timer is set to a first value. A second threshold size could be used to discriminate between ACKs and last response data packets in the case of data response fragmentation. ACKs preferably have a same or near similar size in terms of byte length. Correspondingly, if the data packet size exceeds the second threshold size but not the first threshold size, it is probably the last response data packet and the timer is set to a second value that is preferably smaller than the first value. If the data packet size, however, is equal to or below the second threshold size, i.e. probably an ACK, a third, different timer value can be used.

This can of course be extended to a case with a finer division of threshold sizes to more than two different thresholds.

In a preferred embodiment, the timer is counted down as time lapses. This means that a higher set timer value will lead to a longer period of time until the timer reaches the predefined stop value, preferably zero, and correspondingly a longer period of prevented power down of IMD radio equipment as compared to smaller timer values. If the timer is instead counted up as time lapses, a larger data packet size preferably implies a smaller timer value and thereby a longer period until the timer reaches the predefined stop value as compared to smaller data packet sizes.

The timer processor 140 preferably performs an investigation of the current timer value each time it gets a size parameter from the processor 130. The investigation is conducted to determine whether the current timer value is larger or smaller than the value the timer should be set to by the timer processor 140 based on the received size parameter. Thus, if the current timer value is equal to $T_X$ and the size parameter indicates that the timer should be set to a value $T_Y$, the timer processor 140 resets the value of the timer to $T_Y$ if $T_Y>T_X$ but otherwise, i.e. $T_X \geq T_Y$, it let the timer have its current value $T_X$. For instance, if the IMD sends three response data packets as mentioned above the timer processor 140 preferably first sets the timer to the first, higher value once the first data packet has been received and processed by the size processor 130 since the timer had in this case the predefined stop value, e.g. zero, as current value as starting value. When the second data packet is received and its size (equal to maximum data packet size) has been determined by the size processor 130, the timer processor 140 investigates whether the current timer value is lower than the first value. It is not unlikely that the current timer value is indeed lower than the first value as the timer might have been counted down partly towards the predefined stop value. The timer processor 140 therefore resets the timer once more to the first value. Correspondingly, when the third and last data packet is received, its smaller size indicates that a timer value equal to a second, smaller value should be used.

The timer processor 140 therefore investigates whether the current timer value is larger or smaller than the second value. In the former case, no updating of the timer value is performed. However, if the current value is smaller than the second value, the timer is set to the second value by the timer processor 140.

In an alternative embodiment, the timer processor 140 resets the timer each time it gets a size parameter from the processor 130. Thus, in this embodiment no investigation of the current timer value is performed before resetting the timer. For instance, if the IMD sends three response data packets as mentioned above the timer processor 140 preferably first sets the timer to the first, higher value once the first data packet has been received and processed by the size processor 130. Correspondingly, the timer processor 140 sets the timer to the first value once more when the second data packet is received and its size (equal to maximum data packet size) has been determined by the size processor 130. It is likely that the timer has then not yet counted down to the predefined stop value so the deactivation period is once more started anew.

Correspondingly, when the third and last data packet is received, the timer is now reset by the timer processor 140 to the second, smaller timer value regardless of its actual value. A shorter or no deactivation period then runs.

In yet an alternative but less preferred embodiment, the timer processor 140 does not reset the timer but instead adds the first or second value to the current value of the timer when a data packet is processed by the size processor 130. Such an approach may, however, cause unnecessary long deactivation period after reception of the last response data packet as the timer value can then have been accumulated to quite large value if several response data packets have preceded the last response data packet.

A further embodiment for updating the timer by the timer processor 140 investigates the current timer value as previously described above. However, in this case the timer processor 140 resets the timer if the current timer value is larger than the value the timer should have according to the size parameter. Thus, if the suggested new timer value is smaller than the current value, the timer is reset to the smaller new timer value.

In the foregoing, data packet sizes have been used to discriminate between response/request data packets and ACKs. If the data processing unit and the IMD are configured for generating and transmitting not acknowledgements (NACKs) if a received data packet is not decodable, the size-based discrimination can likewise be used to identify such NACKs since they have sizes in the same range as ACKs, i.e. generally significant smaller than response/request data packets.

As was mentioned in the background section, a particular embodiment of a power save algorithm can be based on the periodicity of the IEGM stream from the IMD. In that embodiment, the data requests generated by the data processing unit and forwarded to the IMD through the communication unit 100 preferably relates to other data besides IEGM data. The response data collected by the IMD is other diagnostic data than IEGM samples and/or device data. The transmission of request/response data packets and ACKs are then preferably scheduled to occur in the timer period between successive IEGM messages.

Figure 4:
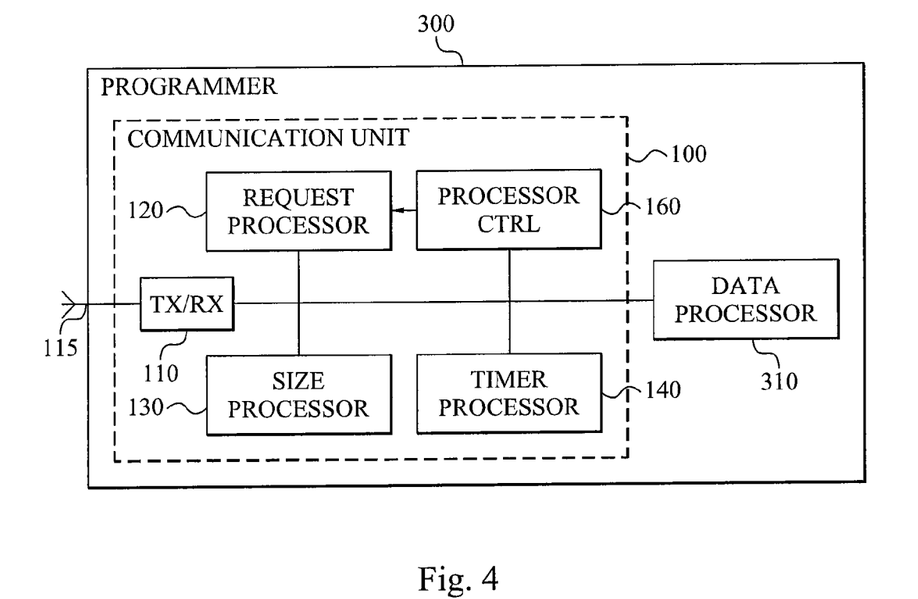
FIG. 4 is a schematic block diagram of a programmer according to an embodiment.

FIG. 3 is a schematic illustration of the main functionalities in a communication unit 100 as used in the data communication system illustrated in FIG. 1. In FIG. 4, which corresponds to the data communication system of FIG. 2, the communication unit 100 and the data processor 310 are implemented in the same device, such as a programmer 300. Generally, no dedicated I/O unit is therefore needed but can of course be used between the communication unit 100 and the data processor 310.

The units 110-170 of the communication unit 100 may be provided as hardware or a combination of hardware and software. Alternatively, these units of the communication unit 100 are implemented in software. In such a case, a computer program product implementing the communication unit 100 or a part thereof comprises software or a computer program run on a general purpose or specially adapted computer, processor or microprocessor. The software includes computer program code elements or software code portions illustrated in FIG. 3 or 4. The program may be stored in whole or part, on or in one or more suitable computer readable media or data storage means such as magnetic disks, CD-ROMs, DVD disks, USB memories, hard discs, magneto-optical memory, in RAM or volatile memory, in ROM or flash memory, as firmware, or on a data server.

The timer set by the timer processor 140 can automatically count down or up as time lapses until it reaches the predefined stop value, at which time the processor controller 160 once more activates the power down request processor 120 to generate the power down request.

Figure 5:
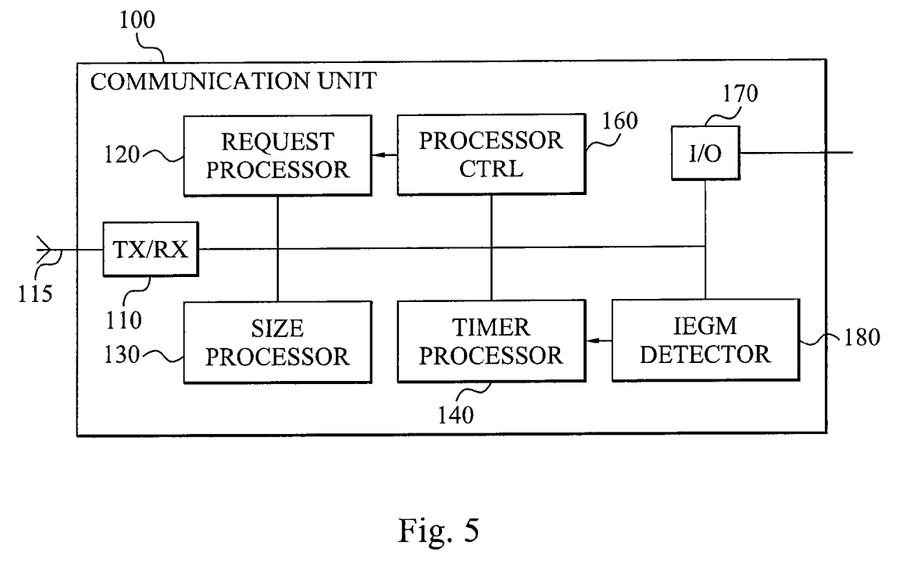
FIG. 5 is a schematic block diagram of a communication unit according to another embodiment.

FIG. 5 illustrates an embodiment of the communication unit in FIG. 3 that uses a more dynamic timer mechanism. If the RF communication performance is quite bad between the communication unit 100 and the IMD, it might require several retransmissions of request and response data packets until these are successfully received by the other party. In such a case the timer might reach the predefined stop value before the IMD has successfully been able to transmit all response data to the communication unit 100. It would therefore be advantageous to have timer counting down/up that is adapted based on the RF communication performance. This is achieved by the communication unit 100 as illustrated in FIG. 5.

The communication unit 100 comprises in this embodiment an IEGM detector 180 for detecting the IEGM messages that are sent from the IMD. For instance and depending on the particular device design, IEGM samples can be produced by the IMD every 7.8125 ms. The IMD then preferably buffers a number of such IEGM samples, such as six, prior transmission. The buffering of IEGM samples yields a periodicity of, in this example, $6 \times 7.8125 = 46.875$ ms for the IEGM messages sent from the IMD to the non-implantable communication unit.

This means that ideally a new IEGM message will be sent by the IMD to the communication unit 100 every 46.875 ms. However, if the current communication link is temporarily experiencing high interference levels or low RF quality for some other reason, the time period until a next IEGM message is successfully received by the communication unit 100 may be longer than 46.875 ms due to one or more retransmission trials before being received by the communication unit 100.

Therefore, in this embodiment the timer processor 140 counts down or up the timer with a predefined reduction or increase value each time the receiver 110 successfully receives an IEGM message from the IMD. The timer will therefore in this embodiment be set by the timer processor 140 to a start value when a data packet size has been determined by the size processor 130 and this start value is then counted down with the predefined reduction value, preferably one, for each received IEGM message. Alternatively, the start value is instead counted up with the predefined increase value, preferably one.

The timer mechanism and the temporary deactivation of the power down request processor 120 is automatically prolonged when the current RF communication performance is bad. That is, if there are a lot of RF disturbances then response data packet(s) will be delayed as will the IEGM message as well. This yields to an automatic prolonged timer due to RF interference.

The IEGM detector 180 illustrated in the communication unit 100 of FIG. 5 and the automatic adaptation of the timer mechanism can also be applied to the communication unit illustrated in FIG. 4.

In the foregoing, the communication unit has been described as using one timer for defining the time period during which the power down request processor should be deactivated. The single timer can then be used in connection with only transmitted data packets (request data packets vs. ACKs), with only received data packets (response data packets vs. ACKs) or with both transmitted and received data packets (request data packets, response data packets and ACKs).

Figure 6:
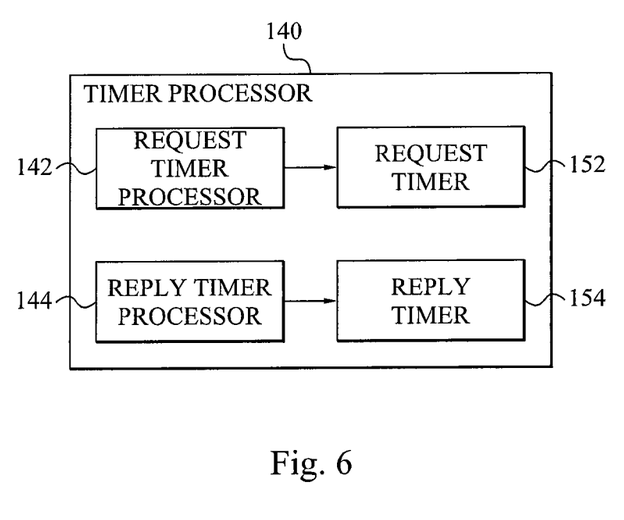
FIG. 6 is a schematic block diagram of a timer processor according to an embodiment.

In a preferred embodiment, the timer processor 140 has access to two timers which is schematically illustrated by the block diagram of FIG. 6. In this embodiment, the timer processor 140 comprises a request timer processor 142 that is configured to set a request timer 152 to a value defined based on the size of a data packet transmitted by the communication unit to the IMD. The request timer processor 142 preferably only operates in relation to request data packets and ACKs originating from the data processing unit. In the case of request data packets having a comparatively large size, the request timer processor 142 sets to the request timer 152 to a first value, whereas for smaller data packets, i.e. ACKs, the request timer 152 is set to a second, preferably smaller value to thereby result in a comparatively shorter deactivation period for the power down request processor.

The timer processor 140 preferably also comprises a reply timer processor 144 that sets a reply timer 154 to a value defined based on the size of data packets received by the receiver of the communication unit. The reply timer processor 144 consequently operates on response data packets and ACKs originating from the IMD. For larger sized (response) data packets, the reply timer processor 144 sets the reply timer 154 to a first value, whereas for smaller sizes, i.e. last response data packet in the case of response fragmentation and ACKs, the reply timer 154 is set to a second, preferably smaller value.

The processor controller of the communication unit is in this embodiment adapted to deactivate and prevent the power down request processor from generating any power down requests if the current value of at least one of the request timer 152 and the reply timer 154 is different from the predefined stop value, preferably zero. Correspondingly, when both the request timer 152 and the reply timer 154 is equal to the predefined stop value, the power down request processor 120 is once more activated and can generate power down requests to trigger power down of the IMD radio equipment in the time period between successive IEGM messages to thereby save power.

The timer processor 140 as illustrated in FIG. 6 can be implemented in any of the communication units illustrated in FIGS. 3 to 5. If implemented in a communication unit that comprises the preferred IEGM detector, both the request timer and reply timer are counted down (or counted up) with the predefined reduction value (predefined increase value) each time the IEGM detector detects an IEGM message received from the IMD.

In a particular example, the request timer processor 142 sets the request timer 152 to a value of 400 ms if the size of a transmitted data packet as determined by the size processor exceeds a defined threshold size and therefore the transmitted data packet is probably a request data packet. Correspondingly, if the size of the transmitted data packet instead would be equal to or smaller than the threshold size as determined by the request timer processor 142, the data packet is likely an ACK and the request timer 152 can then be set to a value of 150 ms.

Correspondingly, the reply timer processor 144 can set the reply timer 154 to a value of 150 ms for large sized data packets received from the IMD, i.e. expectedly reply data packets. A corresponding value of the reply timer 154 for small received data packets could be 100 ms.

The above listed examples of time values set by the request and reply timer processor 142, 144 should merely be seen as illustrative but non-limiting examples of suitable timer values. The particular example is further adapted for usage with a predefined stop value for the two timers 152, 154 or zero. The timers 152, 154 are then counted down as time passes until the value of zero is reached.

If the communication unit comprises an IEGM detector and therefore counts down the request and reply timers 152, 154 upon reception of IEGM messages, the corresponding values of the times 152, 154 as set by the request and reply timer processor 142, 144 can be 8 instead of 400 ms, 3 instead of 150 ms and 2 instead of 100 ms if the reception of an IEGM message is expected 46.875 ms after the preceding IEGM message.

The threshold sizes utilized by the request and reply timer processor 142, 144 to discriminate between predicted request data packets/ACKs and reply data packets/ACKs can be one and the same threshold size or the same set of multiple threshold sizes. Alternatively, different threshold size(s) are used by the request timer processor 142 as compared to the reply timer processor 144.

The threshold size(s) used to discriminate between request/response data packets and ACKs can be determined in a non-inventive manner based on the particular communication protocol defining the communication between the communication unit and the IMD. Thus, from such a protocol the average size of request data packets and ACKs can be determined and the threshold size(s) relating to transmission of data packets by the communication unit can be set to a value that generally allows discrimination between request data packets and ACKs. The maximum allowed size of data packets from the IMD defined in the protocol can be used to set a suitable value to the threshold size(s) applicable for data packets received from the IMD to thereby allow discrimination between ACKs and response data packets.

The IMD and the communication unit can then both comprise a respective medical implant communication service (MICS) chip. In such a case, the transmitter and receiver functions of the communication unit can form part of the MICS chip. Generally, the MICS chip comprises the functionalities for defining the frequency band that is used for the RF-based communication, establishing the radio link, etc. MICS chips are currently available from vendors such as Zarlink Semiconductor.

The power down requests could be communicated between the MICS chips preferably present in both the IMD and the communication unit. The power down requests could then constitute part of the low level messaging of housekeeping commands that never reaches higher levels of processing in the IMD.

In an additional embodiment, the communication unit is further adapted to investigate the house keeping (HK) commands that are communicated between the IMD and the communication unit. These housekeeping commands comprise HK requests from the MICS in the communication unit, which triggers the generation and transmission of HK responses form the IMD MICS. In such a case, the size processor may optionally also investigate the size of the HK messages. The request timer processor 142 and the reply timer processor 144 then preferably each has access to at least two threshold sizes to discriminate between request data packets, ACKs and HK requests and response data packets, ACKs and HK replies, respectfully. Depending on the particular implementation, HK commands could be preconfigured to be of equal size. In such a case, this predefined size of HK commands is associated with a suitable timer value, such as 100 ms or 2 in line with the example values given above. The request or reply timer processor 142, 144 could set or reset the request or reply timer 152, 154 to such a value once the MICS chip of the communication unit receives or transmits a HK command.

In a particular embodiment, the power down request generated by the communication unit to cause a temporary power down of the IMD radio equipment can be transmitted in the form of a HK message. This power down request is, however, preferably excluded from setting any timer values.

Figure 7:
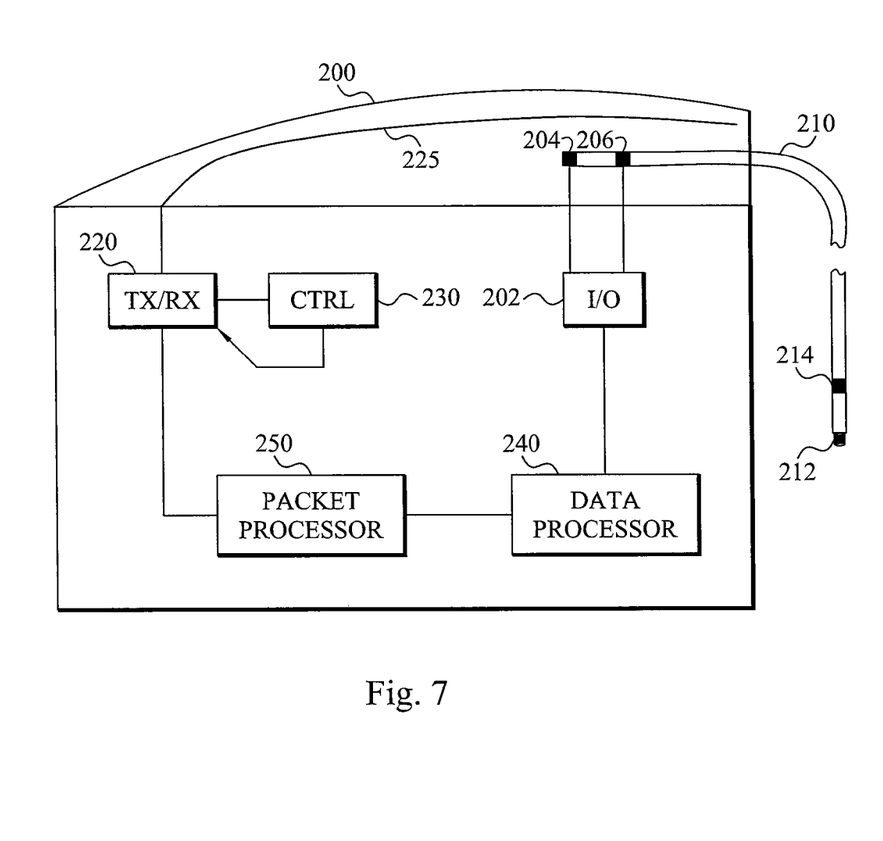
FIG. 7 is a schematic block diagram of an implantable medical device according to an embodiment.

FIG. 7 is a schematic block diagram of an embodiment of an IMD 200 capable of conducting wireless RF-based communication with a non-implantable communication unit. The IMD 200 in particular comprises a receiver 220 connected to a RF antenna 225 and arranged for receiving data transmitted by the communication unit. Correspondingly, the IMD 200 also comprises a transmitter 220 connected to a RF antenna 225 and arranged for wirelessly transmit data packets to the communication unit. The receiver and transmitter 220 can be respective dedicated RF receiver and RF transmitter or represent the receiving branch and the transmitting branch of a combined RF transmitting and receiving unit or transceiver 220. The IMD 200 can include one or more dedicated RF receiver antennas 225 connected to the receiver 220 and one or more dedicated RF transmitter antennas 225 connected to the transmitter 220. However, in most practical implementations one and the same RF antenna or antenna arrangement is connected to both the receiver and transmitter 220 or to the common transceiver.

The IMD 200 comprises a controller 230 connected to the transmitter and/or receiver 220 or the single transceiver. The controller 230 performs a power down of the transmitter and/or receiver 220 or the single transceiver based on a power down request received by the receiver 220 and originating from the communication unit.

In an embodiment, the controller 230 only operates on the transmitter or the transmitting branch 220 of a transceiver. This means that the controller 230 then causes a power down of the transmitter or transmitting branch 220 based on the reception of the power down request. According to another embodiment, the controller 230 only operates on the receiver or the receiving branch 220 of a transceiver and causes a power down thereof based on the power down request. In the former embodiment the receiver or receiving branch 220 of the transceiver is still operational even though the transmitter 220 is powered down by the controller 230. This means that the IMD 200 is potentially capable of receiving data but not transmitting data during the power down period.

In some applications, the IMD 200 cannot in practice transmit any data to the communication unit even though its transmitter 220 is operational but the receiver 220 is powered down. This is in particular relevant when the data transmission from the IMD 200 is controlled by the communication unit as previously mentioned. The IMD 200 and the communication unit can then both comprise a respective MICS chip (not illustrated). The MICS chip of the communication unit can be configured to grant data transmissions made by the MICS chip of the IMD 200. This means that the IMD 200 is then preferably only allowed to transmit data upon such a grant from the communication unit. The reason for such procedure is to prevent collisions that can occur when both the communication unit and the IMD 200 transmit substantially simultaneously, which will lead to high interference levels. In such an application, the IMD 200 cannot receive any transmission grants from the communication unit and is therefore not informed of transmission occasion that it can utilize for data transmission until the receiver 220 once more is powered up. This means that the IMD 200 is not capable of transmitting any data packets even though its transmitter 220 is active if the receiver 220 is powered down.

A further embodiment saves even more power for the IMD 200. In this embodiment, the controller 230 triggers, based on the reception of the power down request, a power down of both the transmitter and the receiver or both the transmitting and receiving branch 220 of the transceiver. This means that the IMD 200 can neither transmit nor receive data during the power down period. Thus, the complete radio equipment of the IMD 200 could therefore be caused by the controller 230 to power down for the power down period.

The preferred embodiments of the present invention relates to an IMD 200 with a controller 230 that powers down the complete radio equipment, i.e. both the transmitter and receiver 220.

The power down of the transmitter and/or receiver 220 by the controller 230 can be effected according to different embodiments. For instance, all the equipment and functionality generally encompassed by the transmitter and/or receiver 220 can be powered down, including, among others, power amplifiers, encoders, decoders, modulators, demodulators, etc. depending on the particular implementation of the transmitter and/or receiver. Alternatively, only some of the equipment and functionality of the transmitter and/or receiver 220 are temporarily powered down by the controller 230. In such a case, the powered down equipment is preferably the ones of the transmitter and/or receiver 220 that typically consumes most power when being active and operational, such as power amplifiers. Power down as disclosed herein consequently covers both a complete shutdown of at least one of the transmitter and the receiver 220 or at least a power down of one of the constituting units in the transmitter and/or receiver 220.

The controller 230 is preferably configured to not only power down the transmitter and/or receiver 220 based on received power down requests but is also responsible for power up the transmitter and/or receiver 220 again. Alternatively, the IMD 200 can comprise a dedicated power down controller and a separate power up controller, although these two preferred functionalities have been housed in the single controller 230 illustrated in the embodiment of FIG. 7. The controller 230 then preferably includes a timer or clock or such a timer or clock is accessible for the controller 230. In such a case, once the controller 230 has identified the received power down request and controlled the transmitter and/or receiver 220 to power down, it preferably starts the timer or identifies the current clock status. Once a defined period of time has lapsed, such as corresponding to the timer reaching a define end value or the clock status has reached a defined value relative the previously identified clock status, the controller 230 triggers a power up of the powered down portion of the transmitter and/or receiver 220. The power down period could be a pre-defined, default value, for instance hard coded in the IMD 200, such as using a timer counting down from a starting value to zero. Alternatively and in order to achieve an adaptation in the power down, the communication unit that compiles and transmits the power down requests to the IMD 200 can determine a length of the power down period that is suitable for the current situation. In such a case, the communication unit preferably includes a notification of the determined power down period in the power down request. The controller 230 retrieves this notification from the received request and triggers a power up once the timer or clock has indicated that the time period defined by the notification has lapsed from the previous, last power down of the transmitter and/or receiver 220.

The IMD 200 also comprises an electrode I/O unit 202 comprising or being connectable to electrode terminals 204, 206. These electrode terminals 204, 206 are arranged in the IMD 200 for electrical connection to respective implantable electrodes 212, 214 preferably arranged on one or more cardiac leads 210. The implantable electrodes 212, 214 are typically provided at a distal end of the cardiac lead 210 and are, in operation, introduced into or attached close to a ventricle or an atrium of the heart.

The electrode I/O unit 202 is electrically connected to the electrodes 212, 214 of the cardiac leads 210 through conductors running in the lead body from the electrodes 212, 214 at the distal end to terminals at the proximal end and through the electrode terminals 204, 206 that are electrically and mechanically attached to the terminals at the proximal end. The electrode I/O unit 202 can also be electrically connected to one or more electrodes that are not provided on the at least one cardiac lead 210. Such an electrode can actually constitute the housing or can of the IMD 200 or at least a portion thereof, which is well known in the art.

The IMD 200 comprises a data processor 240 that is connected to the electrode I/O unit 202. The data processor 240 is provided for recording sets of data samples representing the detected or sensed physiological parameter from the animal body, preferably such a physiological parameter representative of the operation of the heart of the animal body. The sample data is forwarded to the packet processor 250 that is used for organizing the input data into data packets that can be transmitted by the IMD 200.

The data samples are preferably collected by the data processor 240 in response to the reception of a data request from the communication unit.

FIG. 7 merely illustrates the units of an IMD 200 that are directly involved in embodiments as disclosed herein. It is therefore anticipated that the IMD 200 comprises additional units that are not illustrated in the figure and that are not directly involved in the operation of the disclosed embodiments.

The units 202, 220, 230 to 250 of the IMD 200 may be provided as hardware or a combination of hardware and software.

Alternatively, these units of the IMD 200 are implemented in software. In such a case, a computer program product implementing the IMD 200 or a part thereof comprises software or a computer program run on a general purpose or specially adapted computer, processor or microprocessor of the IMD 200. The software includes computer program code elements or software code portions illustrated in FIG. 7. The program may be stored in whole or part, on or in one or more suitable computer readable media or data storage means such as hard discs, magneto-optical memory, in RAM or volatile memory, in ROM or flash memory.

Figure 8:
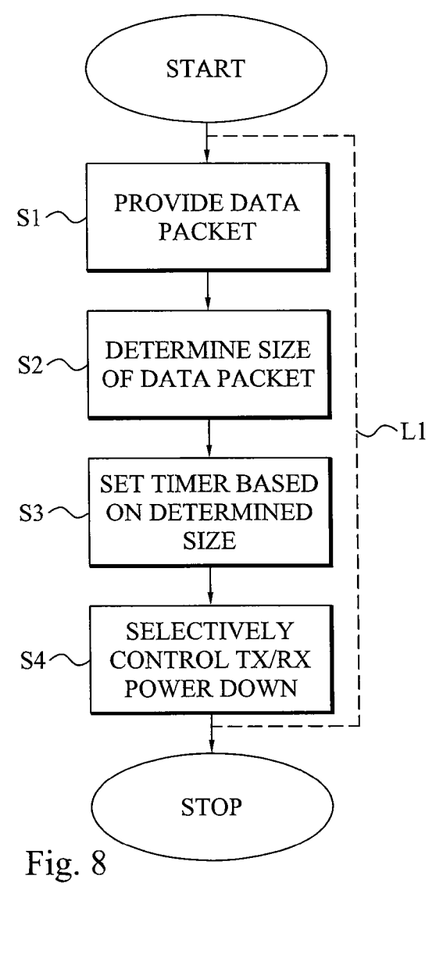
FIG. 8 is a flow diagram illustrating a communication control method according to an embodiment.

FIG. 8 is a flow diagram illustrating a communication control method according to an embodiment. The method generally starts in step S1, where a data packet is provided in the communication unit. The data packet provision of step S1 can be performed according to various embodiments. In an embodiment, the data packet is received from the connected data processing unit and is intended to be wirelessly transmitted by the communication unit to the IMD. An alternative embodiment involves receiving the data packet from the IMD.

A next step S2 determines or estimates the size of the data packet provided in step S1. The size determination preferably involves determining the total size of the data packet in terms of the number of bytes. Alternatively and if the communication unit has functionality for discriminating between payload portion and header/tail portions, the determined size in step S2 could be the size of the payload portion of the provided data packet.

A timer is set in step S3 based on the size determined in step S2. The value of the set timer is further dictated by the determined size of the data packet. In a preferred implementation, the value of the timer is determined based on a comparison of the size with at least one threshold size and in particular depends on whether the size exceeds the threshold size or not.

A next step S4 selectively controls the generation of power down requests defining a power down of the IMD radio equipment based on the current value of the timer. Thus, the current value of the timer determines whether such power down request should be generated or whether the generation of the power down requests should be at least temporarily prevented.

In a preferred implementation, the generation of power down requests is performed periodically with a periodicity that is preferably defined based on the periodicity in generating IEGM messages at the IMD. At each such scheduled power down request generating occasion, the current value of the timer can be investigated to decide whether a power down request can be generated or whether it should be prevented.

The procedure of steps S1 to S3 are preferably conducted each time a new data packet is provided at the communication unit. Furthermore, the selective control is preferably conducted at the above-mentioned scheduled time occasions and can therefore be repeated multiple times, which is schematically illustrated by the line L1. The communication control method can be run even when the IMD has not yet been implanted in the animal or human body, e.g. when investigating or testing its communication equipment.

Figure 9:
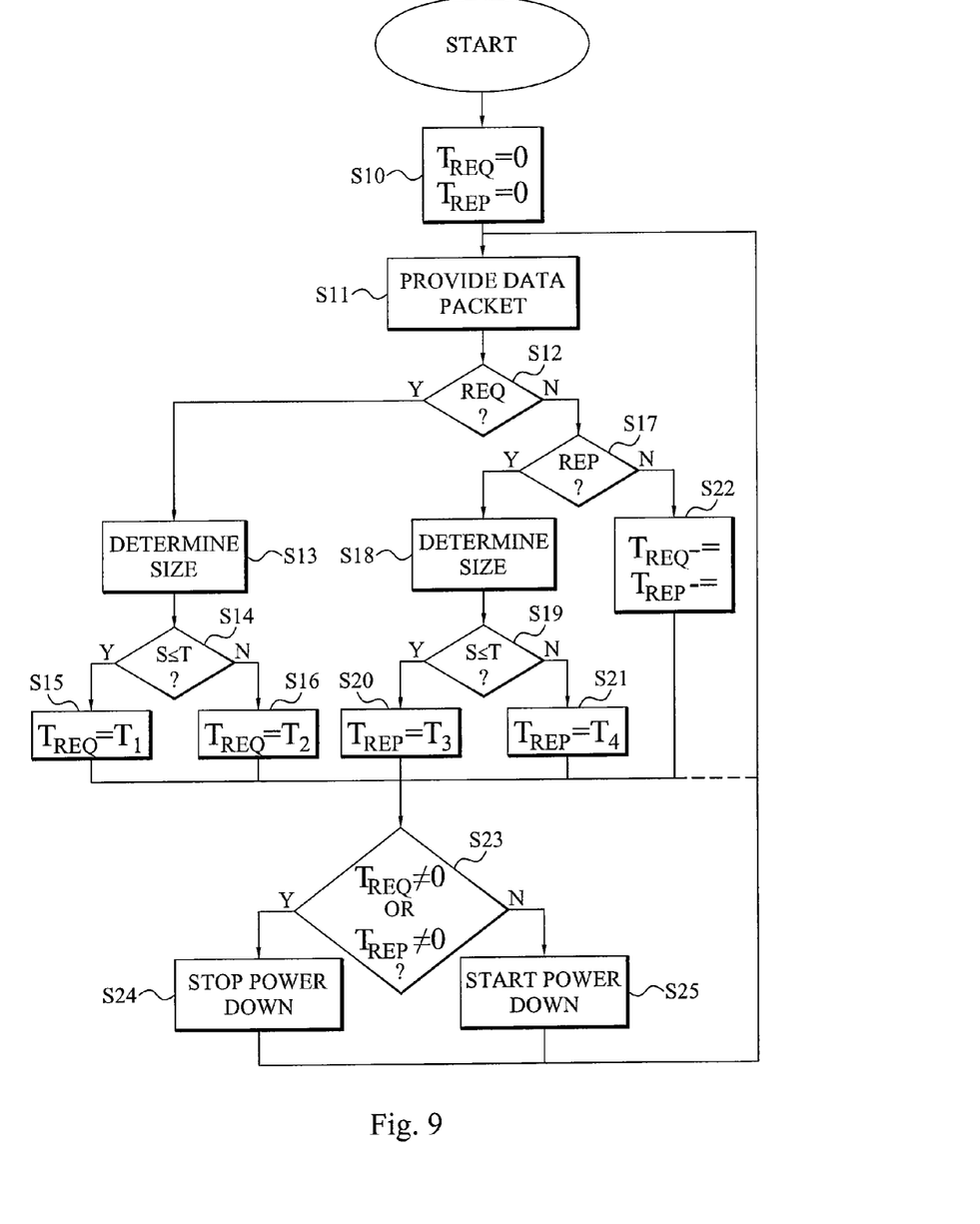
FIG. 9 is a flow diagram illustrating a communication control method according to another embodiment.

FIG. 9 is a flow diagram illustrating a particular implementation of the communication control method in FIG. 8.

The method starts in step S10, where a request timer ($T_{REQ}$) and a response timer ($T_{REP}$) are both set to the predefined stop value of 0. The step S10 is generally performed in connection with starting up a communication session between the IMD and the communication unit to ensure that these timers have the preferred default value that allows running the power down requesting procedure.

A next step S11 is performed once the communication unit receives a data packet either from the IMD or from the data processing unit. Step S11 basically corresponds to step S1 in FIG. 8. Step S12 investigates whether the data packet originates from the data processing unit and consequently can be a data request. If the data packet provided in step S11 originates from the data processing unit the method continues to step S13. This step S13 determines the size (S) of the data packet as previously described in connection with step S2 of FIG. 8. The determined size is compared to a threshold size (T) in step S14. If the determined size of the data packet from the data processing unit exceeds the threshold size the method continues to step S16, where the request timer is set to a second timer value (T2), such as 8. If the size does not exceed the threshold size in step S14, the method instead continues to step S15. Step S15 involves setting the request timer to a first timer value ($T_1$), such as 3.

If the data provided in step S11 does not originate from the data processing unit it therefore originates from the IMD. The method continues to step S17, which investigates whether the data packet from the IMD is a tentative response data packet or an IEGM message. If it is concluded that the data packet is not an IEGM message, e.g. a response data packet or ACK, the method continues to step S18, where the size of the data packet is determined in similarity to step S13. If the size exceeds a threshold size, which may be the same threshold size as in step S14 or another threshold size, the method continues from step S19 to step S21. Step S21 sets the value of the response time to a fourth timer value ($T_4$), such as 3. If the size does not exceed the threshold size, the response timer is instead set to a third value ($T_3$) in step S20, such as 2.

Optionally, steps S15, S16, S20 and S21 first investigates the current value of the timers in order to determine whether the timers should be set to the value $T_1$, $T_2$, $T_3$ or $T_4$ based on whether the current timer value exceeds the value $T_1$, $T_2$, $T_3$ or $T_4$.

In all of steps S15, S16, S20 and S21 the method then continues to step S23 or back to step S11. Step S23 is triggered when it is time to check whether a power down request can be issued. Step S23 investigates the current values of the request and response timers. If any of them are not equal to zero, power down of the IMD should be postponed and the method continues to step S24, where the processor controller of the communication unit prevents the power down request processor from generating a power down request.

If, however, both timers are zero, the method continues to step S25, where a power down request is generated and transmitted to the IMD to cause a temporary power down of the radio equipment.

The generation of the power down request in step S25 can, in an embodiment, be performed as soon as both timers are zero. Alternatively, power down requests should be generated periodically at scheduled time instances. In such a case, step S23 is performed during each such time instance and if both timers are then zero, the power down procedure is started in step S25.

If the data packet received from the IMD instead is determined to be an IEGM message in step S17, the method continues to step S22, which decrements the request and response timers with one. The method then continues to step S23 or to step S11.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

What is claimed is:

1. A communication control method comprising:
   determining a size of a data packet received from an implantable medical device or transmitted to the implantable medical device;
   setting a timer to a value defined based on the size;
   selectively controlling the generation of power down requests defining a power down of at least one of a transmitter and a receiver of the implantable medical device based on a current value of the time;
   wherein the setting comprises:
      setting the timer to a first predetermined value if the size exceeds a threshold size; and
      setting the timer to a second predetermined value if the size is below the threshold size, the first predetermined value being larger than the second predetermined value; and
   based on the received or transmitted data packet, having the implantable medical device provide therapy to a patient.

2. The communication control method according to claim 1, wherein the selectively controlling comprises stopping the generation of the power down requests if the current value of the timer is different from a predefined stop value.

3. The communication control method according to claim 1, wherein the selectively controlling comprises starting the generation of the power down requests if the current value of the timer is equal to a predefined stop value.

4. The communication control method according to claim 1, and further comprising:
   receiving an intracardiac electrogram, IEGM, message from the implantable medical device; and
   reducing the value of the timer with a predefined reduction value in response to the reception of the IEGM message.

5. The communication control method according to claim 1, further comprising receiving the data packet received from the implantable medical device or transmitting the data packet to the implantable medical device in a time window occurring between reception of two successive intracardiac electrogram, IEGM, messages originating from the implantable medical device.

6. The communication control method according to claim 1, further comprising comparing the current value of the timer with the value defined based on the size, wherein the setting comprises setting the timer to the value defined based on the size if the value defined based on the size is larger than the current value of the timer.

7. The communication control method according to claim 1, wherein the setting comprises:
   setting a request timer to a value defined based on the size of a data packet transmitted to the implantable medical device; and
   setting a reply timer to a value defined based on the size of a data packet received from the implantable medical device.

8. The communication control method according to claim 7, wherein the selectively controlling comprises stopping the generation of the power down requests if the current value of at least one of the request timer and the reply timer is different from a predefined stop value.

* * * * *